US006824682B2

(12) United States Patent
Branson

(10) Patent No.: US 6,824,682 B2
(45) Date of Patent: Nov. 30, 2004

(54) SYSTEM AND METHOD FOR EXTRACTING ENERGY FROM AGRICULTURAL WASTE

(75) Inventor: Jerrel Dale Branson, Ridgefield, CT (US)

(73) Assignee: Best Biofuels LLC c/o Smithfield Foods, Inc., Smithfield, VA (US)

( * ) Notice: Subject to any disclaimer, the term of this patent is extended or adjusted under 35 U.S.C. 154(b) by 77 days.

(21) Appl. No.: 10/320,744

(22) Filed: Dec. 17, 2002

(65) Prior Publication Data

US 2003/0111410 A1 Jun. 19, 2003

Related U.S. Application Data

(60) Provisional application No. 60/340,491, filed on Dec. 18, 2001.

(51) Int. Cl.[7] ............................. C02F 3/28; C07C 27/00; C12M 1/00; F02C 3/00
(52) U.S. Cl. ........................ 210/603; 210/259; 518/700; 518/713; 518/714; 435/262.5
(58) Field of Search .............................. 210/603, 613, 210/259; 71/10, 21, 23; 518/700, 713, 714; 435/262, 262.5

(56) References Cited

U.S. PATENT DOCUMENTS

| | | | | |
|---|---|---|---|---|
| 3,326,956 A | * | 6/1967 | Davies et al. ............... | 518/713 |
| 3,698,881 A | | 10/1972 | White | |
| 4,183,807 A | | 1/1980 | Yoshizawa et al. | |
| 4,289,625 A | | 9/1981 | Tarman et al. | |
| 4,339,546 A | * | 7/1982 | Randalls ..................... | 518/704 |
| 4,372,856 A | | 2/1983 | Morrison | |
| 4,705,673 A | * | 11/1987 | Capobianco et al. ....... | 423/226 |
| 4,721,569 A | | 1/1988 | Northrop | |
| 4,919,912 A | * | 4/1990 | Taggart et al. ........... | 423/574.1 |
| 5,121,600 A | | 6/1992 | Sanders et al. | |
| 5,185,075 A | | 2/1993 | Rosenberg et al. | |
| 5,427,762 A | * | 6/1995 | Steinberg et al. ........ | 423/449.1 |
| RE35,377 E | * | 11/1996 | Steinberg et al. ........... | 518/704 |
| 5,713,965 A | | 2/1998 | Foglia et al. | |
| 5,861,051 A | * | 1/1999 | Critchfield et al. ........... | 95/172 |
| 5,922,092 A | | 7/1999 | Taylor | |
| 6,015,440 A | | 1/2000 | Noureddini | |
| 6,114,400 A | * | 9/2000 | Nataraj et al. .............. | 518/715 |
| 6,133,328 A | * | 10/2000 | Lightner ..................... | 518/700 |
| 6,299,774 B1 | * | 10/2001 | Ainsworth et al. ......... | 210/603 |
| 6,340,581 B1 | * | 1/2002 | Gaddy ........................ | 435/140 |
| 6,410,283 B1 | | 6/2002 | Rehmat et al. | |
| 6,440,057 B1 | | 8/2002 | Ergun et al. | |

FOREIGN PATENT DOCUMENTS

GB       2375353      * 11/2002

OTHER PUBLICATIONS

International Search Report dated Mar. 13, 2003, for application No. PCT/US02/40116, filed Dec. 17, 2002.

* cited by examiner

Primary Examiner—Fred G. Prince
(74) Attorney, Agent, or Firm—Hunton & Williams

(57) ABSTRACT

The present invention relates to a process and apparatus for processing agricultural waste to make alcohol and/or biodiesel. The agricultural wastes are subjected to anaerobic digestion which produces a biogas stream containing methane, which is subsequently reformed to a syngas containing carbon monoxide and hydrogen. The syngas is converted to an alcohol which may be stored, sold, used, or fed directly to a reactor for production of biodiesel. The solids effluent from the anaerobic digester can be further utilized as slow release, organic certified fertilizer. Additionally, the wastewater from the process is acceptable for immediate reuse in agricultural operations.

21 Claims, 6 Drawing Sheets

SYSTEM AND METHOD FOR EXTRACTING ENERGY FROM AGRICULTURAL WASTE

This application claims benefit of U.S. Provisional 60/340,491 filed Dec. 18, 2001

BACKGROUND OF THE INVENTION

1. Field of Invention

The present invention relates to a combination of systems and methods for converting agricultural waste, such as animal manures, to alcohols and methyl esters, with the concurrent generation of emission-free electricity and reuse of the wastewater produced. The systems and methods of the invention provide efficient and sanitary disposal of agricultural waste and produce useable energy and fertilizer.

2. Description of Related Art

Small, family farms are steadily being replaced by larger integrated confinement corporate agricultural operations. Such large agricultural operations often utilize confinement barns for concentrated housing of large numbers of livestock units, such as swine, dairy cattle, or poultry. The swine and poultry industry have tended to concentrate such operations in a few counties nationwide. Some individual counties may contain greater than one million hogs. The meat production economies of scale enjoyed by such corporate farmers are offset by the pollution problems arising from the handling and treatment of the collected waste and other manures from such operations. Not only do the collected agricultural waste streams have concentrations of nitrogen, phosphorus, bacteria and pathogens, but also noxious odors are a standard of current operations. In addition, there is a high potential for releases from the wastewater containment lagoons during periods of excessive rainfall, greatly endangering surrounding waterways and neighboring properties.

Currently such concentrated farming operations treat their wastewater with a combination of aerobic and anaerobic digestion in open lagoons due to its simplicity and lower capital costs. In this system the raw wastewater is simply discharged from the confined animal facility into open lagoons where the waste undergoes natural anaerobic digestion, followed by aerobic polishing. During this process greater than forty noxious gases, including ammonia, hydrogen sulfide and methane, are emitted to the atmosphere in an unregulated fashion. Certain regulations require a residence time for such wastewater in an open lagoon of 180 days for more complete digestion. Adjacent properties suffer from both the odors and the runoff of the sprayfield discharge of the treated effluent. In addition, studies have shown that lagoons leak causing pollution problems in groundwater, rivers, estuaries and lakes in areas of high concentration of confined animal farming.

In the case of swine manure treated in standard anaerobic lagoons, the liquid effluent has nutrient characteristics including high levels of biological oxygen demand ($BOD_5$), (total amount of biological oxygen demand measure over a five day period). Total Nitrogen (TN) and Phosphorus (P) than can be reduced to permitted levels by anaerobic digestion alone. Even with bacterial digestion, significant amounts of sludge accumulation in an anaerobic lagoon may cause it to reach capacity quickly and fail to provide long term effective wastewater treatment.

Swine produce two to four times as much waste, per hog, as the average human. In North Carolina alone, hogs produce about 9.5 million tons of manure per year. Each swine producing farm utilizes a great deal of land for spreading the highly concentrated wastewater following digestion as very often no discharge is permitted from animal waste facilities. Regulations require farms to utilize increasingly large areas as sprayfields for this effluent as residual concentrations of nutrients may cause permanent damage to the soil and groundwater in these areas. Some states have contemplated a moratorium on new concentrated farming facilities due to the agricultural wastewater treatment problems. In North Carolina, owners of existing agricultural wastewater treatment facilities constructed prior to Dec. 31, 1993, must register with the state and have their animal waste plan certified by a third party.

The initial application of anaerobic digestion of organic waste streams was the septic tank, invented in 1895. Beginning in the 1950's, anaerobic digestion processes were applied to livestock slaughtering wastewaters. This anaerobic contact process made use of a reactor tank in which contact between anaerobic microorganisms and wastewater occurs. The wastewater then flows through a vacuum degasifier to remove dissolved gas to enhance solids settling and then on to a separate solids separation unit in which biomass solids settle to the bottom for recycling to the contact tank. In these existing systems, multiple vessels are required which have a high capital investment, and there are inherent inefficiencies in multi-step processes. Additionally, the biogas produced in such systems typically is released to the atmosphere.

U.S. Pat. No. 4,372,856 discloses a method and apparatus for anaerobic digestion of agricultural waste to produce biogas containing mainly methane and carbon dioxide. The method utilizes ammonia generated during the anaerobic digestion to strip hydrogen sulfide from the biogas containing methane and carbon dioxide. U.S. Pat. No. 5,922,092 discloses a gasification system whereby solid wastes, including agricultural waste, are contacted with gas in a thermal reactor. A by-product of this method includes diesel fuel, asphaltic materials, liquified gases and others. U.S. Pat. No. 6,410,283 discloses a method for generating electricity by anaerobic digestion of sewage sludge. The disclosures of these patents are incorporated by reference herein in their entirety.

Methane-rich gases have been converted to synthesis gases by reformation to the basic elements of such feedstock for many years. The reformation of methane-rich gases at elevated temperatures in the presence of steam and a heterogeneous catalyst also has been accomplished for a number of years. The efficacy of such processes has enhanced by the introduction of Carbon Dioxide ($CO_2$) from external sources to the methane-rich gas stream. The addition of more carbon atoms from external resources serves to create a more balanced Hydrogen ($H_2$) and Carbon Monoxide (CO) product of the reforming process.

Converting synthesis gas to methanol by passing the synthesis gas over a heterogeneous catalyst at controlled pressure and temperature has been accomplished on a commercial scale for a number of years. The mixed alcohol product of this process is used primarily as feedstock for the production of formaldehyde or methyl tert-butyl ether (MTBE). Producing methyl esters from mixed alcohols in combination with a catalyst and fats or oils under heat and pressure has been accomplished for a number of years on a commercial scale. Such products also do not qualify as a fully renewable product.

Methods of treating wastewater rich in nutrients are disclosed, for example, in U.S. Pat. No. 626,644 to Northrop, U.S. Pat. No. 4,721,569 to Northrop, U.S. Pat. No. 4,183,807 to Yoshizawa, et a.l and U.S. Pat. No. 5,185,079 to Dague. Methods of utilizing agricultural waste or biomass as fuel for electrical generation are disclosed, for example, in U.S. Pat. No. 5,121,600 to Sanders, et al. Methods of converting methanol and fats or oils to methyl esters and biodiesel are disclosed in, for example, U.S. Pat. Nos. 5,713,965 to Foglia, et al., 6,015,440 to Noureddini, and 6,440,057 to Nurhan, et al. The disclosures of these patents are incorporated by reference herein in their entirety.

Notwithstanding the existence of these known treatment and conversion systems, there is a need for an agricultural wastewater treatment system that is capable of digestion of a higher organic solid fraction and conversion of the produced biogas to a transportable, liquid energy product on a continuous basis. Efforts to improve extant methods and apparatus continue.

The description herein of disadvantages associated with known processes and apparatus is by no means intended to limit the scope of the invention to embodiments that exclude the known processes and apparatus. Indeed, certain embodiments of the invention may include some or all aspects of known processes and apparatus, in some instances without suffering from the above-described disadvantages.

SUMMARY OF THE INVENTION

It is a feature of an embodiment of the present invention to provide an apparatus, methodology and system to reduce the problem of noxious odors at individual farms by using concentrated anaerobic digestion as a portion of a continuous treatment system. Another feature of the invention is to provide a method for digestion of high strength biosolids in a centralized digestion facility in order to minimize the negative impact of concentrated farm operations on groundwater and adjacent surface water.

An additional feature of the invention is to provide an apparatus and method of treatment of animal manures that will reduce, eliminate, or ameliorate spray field or land application of the effluent of the digester process. Another feature of the present invention is to create a slow release fertilizer as a by-product of the digester system that retains the maximum nutrient value for slow-release topical application.

Another feature of the present invention is to create a synthesis gas from the biogas product of anaerobic digestion of agricultural or animal waste streams that serves as a feedstock for alcohols, petrochemicals and pharmaceuticals. Yet another feature of the present invention is to create a methyl ester from totally renewable raw materials for use as a plastics additive and a biodiesel motor fuel.

Other features of the invention include creating emission-free electricity generation form the capture of waste heat from the synthesis gas manufacturing process, converting renewable resource-based synthesis gas to transportable, liquid energy products as both an end product and as feedstock for further renewable energy processes, and providing an integrated system for the reduction of agricultural or animal wastes and their conversion to energy and feedstock products in a positive economic manner.

The present invention is includes a system, method and apparatus for treating agricultural and/or animal waste streams and their conversion to synthesis gas, electricity and liquid energy feedstock products. The present invention is intended to provide for the near complete digestion of high strength biosolids and their economic conversion to renewable energy products with a concurrent, significant reduction in the environmental impact of concentrated farming operations.

In accordance with these and other features of the invention, there is provided a method for treating agricultural wastes comprising anaeorbic digesting a mixture of at least agricultural waste and water to yield solids and a biogas including methane and carbon dioxide, reforming the biogas including methane and carbon dioxide to a syngas including carbon monoxide and hydrogen in a steam reformation process, and then converting the syngas containing carbon monoxide and hydrogen to methanol in an alcohol conversion process.

In accordance with an additional feature of the invention, the methanol produced in the alcohol conversion process then is reacted with natural fats and/or oil to produce glycerine and methyl esters, and then the glycerine and methyl esters are separated. Another feature of the invention resides in digesting concentrated agricultural waste having a solids content of greater than about 4–6% that is heated prior to digestion. An additional preferred feature of the invention is that the syngas can be converted to methanol without the need to add carbon dioxide or additional carbon monoxide other than that present in the syngas.

In accordance with another feature of the invention, there is provided a system for treating agricultural waste comprising an anaerobic digestion apparatus to digest agricultural waste and create solids and a biogas, a biogas reformation apparatus to reform the biogas via the use of steam into a syngas including carbon monoxide and hydrogen, and an alcohol conversion apparatus to convert the carbon monoxide and hydrogen into methanol.

In accordance with an additional feature of the invention, the system further includes a reaction apparatus to react methanol produced in the alcohol conversion apparatus with natural fats and/or oil to produce glycerine and methyl esters, and a separation apparatus to separate the glycerine and methyl esters.

These and other features of the invention will become readily apparent to those skilled in the art upon reading the detailed description that follows.

BRIEF DESCRIPTION OF THE DRAWINGS

For a more complete understanding of the nature and features of the present invention, reference should be made to the following detailed description taken in connection with the accompanying drawings in which.

DETAILED DESCRIPTION OF PREFERRED EMBODIMENTS

Throughout this description, the expression "agricultural waste" denotes in general farming waste, including animal carcasses, vegetation, animal waste, and preferably denotes animal waste in the form of animal manure. Agricultural waste typically is digested in concentrations of about 1% solids by weight, and consequently, the phrase "concentrated agricultural waste" denotes agricultural waste that has a higher solids content than conventional waste, and preferably denotes agricultural waste having greater than about 4% solids, more preferably greater than about 5% solids.

In particularly preferred embodiments the invention encompasses the conversion of the organic fraction of agricultural animal manures to alcohols by (1) initially creates biogas with constituents of approximately 65% methane ($CH_4$) and carbon dioxide ($CO_2$) by anaerobic digestion of high strength biosolids (>8% by volume) in a covered lagoon digester capable of capturing all of the gaseous discharge of the process; (2) the captured biogas is scrubbed for removal of hydrogen sulfide ($H_2S$) to a constituent level of ≦50 ppm prior to introduction to a steam reformation unit for conversion to synthetic gas; (3) the produced synthetic gas with constituents of approximately 1 mol Hydrogen ($H_2$) for each 1 mol Carbon Monoxide (CO) is cooled by air/air heat exchangers prior to introduction into an alcohol conversion loop utilizing a heterogeneous catalyst for conversion to raw alcohol; (4) the raw alcohol is then distilled into its separate alcohol fractions for sale or for use as a raw material in the production of biodiesel; (5) the raw alcohol is blended with fats or oil and a catalyst for the production of methyl esters which may be used as biodiesel motor fuel or other applications (6) concurrent with the cooling of the synthesis gas the waste heat is captured as the thermal energy source for an integrated air turbine electric generation unit. The effluent from the anaerobic digester is further utilized as slow release, organic certified fertilizer. Additionally, the wastewater from the process is acceptable for immediate reuse in agricultural operations.

The invention relates in general to a system, method, and apparatus for creating methanol and/or methyl esters from agricultural waste. In accordance with the method and system, agricultural wastes are digested in an anaeorbic digestor to yield solids and a biogas including methane and carbon dioxide. The biogas containing at least methane and carbon dioxide is reformed to a syngas including carbon monoxide and hydrogen in a steam reformation process, and then the syngas containing carbon monoxide and hydrogen is converted into methanol in an alcohol conversion process. This methanol then may be stored and sold as a fuel source, or it can be reacted further with natural fats and oils to produce methyl esters and glycerine, which subsequently can be separated. The methyl esters then can be use as a source of biodiesel.

Figure 1:
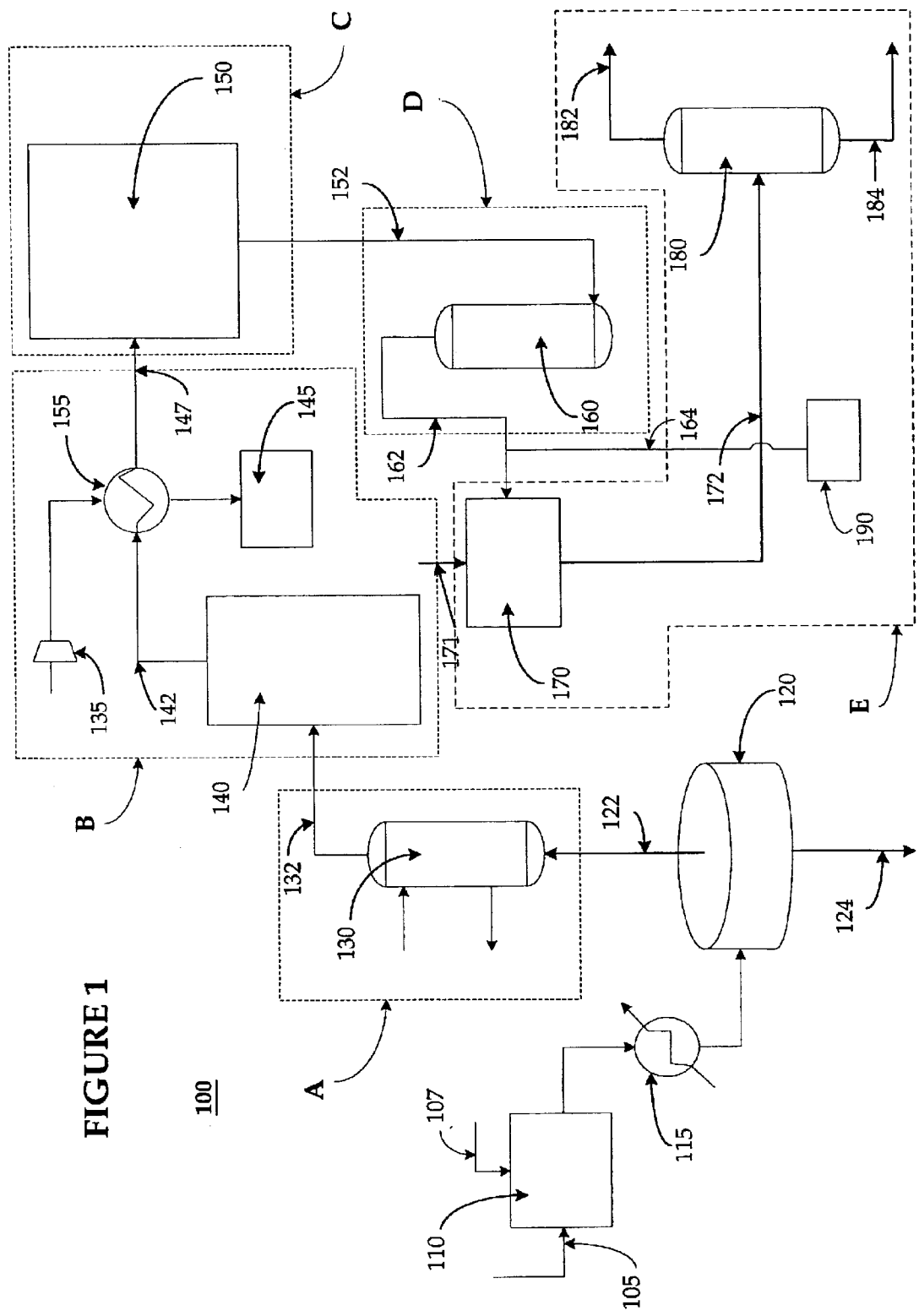
FIG. 1 is a flow diagram illustrating a preferred embodiment of the present invention whereby agricultural waste is treated to produce methanol and biodiesel.

Turning now to FIG. 1, a concentrated waste stream 105 containing agricultural waste having a solids content of as high as 30% is contacted with water via stream 107 in vessel 110 to produce an agricultural waste stream having a solids content of from about 4% to about 8%. This waste stream then can be heated in heat exchanger 115 and then introduced to an anaerobic digestion system 120 in which the digestion of the organic solid fraction will occur. The high strength biosolids anaerobic digestion system 120 of the invention preferably accommodates total solids up to 8% by volume for highly efficient digestion and low effluent discharge in a single vessel. The designed hydraulic retention time for the anaerobic digestion system 120 preferably is less than 30 days. The anaerobic digestion system 120 thereby allows the introduction of high lipid or proteinaceous animal waste into the digestive process from non-farm sources, which serves to increase the production of biogas 122. Solids may be extracted periodically from anaerobic digestion system 120 via stream 124 and used, for example, as fertilizer.

The biogas stream 122 preferably is harvested from the anaerobic digestion system 120 by means of a vacuum blower arrangement that causes the raw biogas to pass through a solvent vessel 130 that purifies the biogas stream 122 by removing entrained hydrogen sulfide ($H_2S$) to concentrations ≦50 ppm, and produce a cleaned biogas stream 132. The cleansed biogas stream 132 then preferably is introduced into a steam reformer apparatus 140 for conversion to a primary product of syngas 142 composed primarily of hydrogen ($H_2$) and carbon monoxide (CO) through elevated temperatures in the presence of a heterogeneous catalyst. The syngas preferably is then cooled by air/air heat exchanger(s) 155 to produce a cooled syngas stream 147 prior to introduction to the alcohol conversion apparatus 150.

The air/air heat exchanger(s) preferably lower the syngas temperature from approximately 1575° F. to approximately 100° F. on a continuous flow basis. The cooling medium preferably is ambient air which is compressed to 5 lbs/sec in compressor 135, and condensed steam water vapor for cross exchange with the hot synthesis gas. Following absorption of the maximum available heat, the heated air fluid passes to electricity generation apparatus 145. The heated air fluid preferably passes over a turbine wheel that is spun to approximately 30,000 rpm by the expansion of the heated fluid across its blade field. This turbine wheel powers a standard electric generator that can be used to provide power to the overall system.

The cooled syngas product 147, which contains primarily carbon monoxide and hydrogen, then is introduced to an alcohol conversion apparatus 150 at approximately 100° F. In the presence of a heterogeneous catalyst, such as ZnO—$Cr_2O_3$ or CuO—ZnO—$Al_2O_3$, the syngas constituents of $H_2$ and CO are converted to methanol:

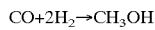

$$CO+2H_2 \rightarrow CH_3OH$$

The alcohol conversion apparatus 150 is capable of creating approximately 75% methanol ($CH_3OH$) and 25% water ($H_2O$) on a continuous basis. The raw alcohol stream 152 then preferably is delivered to a distillation unit 160, more preferably two distillation towers (see, FIG. 5) in which the low humidity methanol product 162 is driven off by heat and distilled, and a portion of the product stream may be diverted via stream 164 into storage tank(s) 190 for sale as an end product or a raw material for further energy products.

All or a portion of the methanol product 162 may be introduced into a heated reactor 170 in presence of natural fats or oils via stream 171 and a catalyst for the process of transesterification. The process produces a transesterification product stream 172 comprising crude glycerine and methyl esters. The transesterification product stream 172 then may be fed to separator 180 to separate these two products into methyl esters 182, and glycerine 184, and deliver them to individual storage vessels. The glycerine may be sold as crude feedstock for production of cosmetics, soaps, petrochemicals and food additives. The methyl ester may be sold as an additive for the petrochemical or plastics industries or as a biodiesel motor fuel. In the instance of the biodiesel, the product will be a totally renewable motor fuel.

Those skilled in the art will appreciate that many of the preferred unit operations described herein for effecting the desired reaction, conversion, reformation, etc. may be replaced with other unit operations without significantly departing from the spirit and scope of the invention. For example, a distillation column having (n) stages with one or more condensers may be described as useful for effecting a separation. Other separation apparatus may be used including multiple distillation columns, liquid/liquid extraction units, fluidized bed or packed column separators, and the like.

A preferred anaerobic digestion system 120 operates as a combined pre-treatment and secondary treatment facility, thus significantly reducing the size of the facility and the amount of external thermal energy required to assure optimum operation. The system preferably comprises an in-ground anaerobic digester especially designed to accommodate high strength biosolid wastes (concentrations of solids between 8% and 10%). The design reduces the level of Biological Oxygen Demand ("BOD") in the waste stream and through anaerobic digestion generates the methane-rich biogas. A rotary vane blower can be utilized to 'harvest' the produced biogas from within the space between the cover and media of the digester on a continuous basis. Because of the BOD reduction, aerobic post-treatment requires reduced aeration input, thus lowering the energy demand of the system. In addition to the degradation of the organic compounds in the raw animal manures and/or non-farm wastes, the digester can be used for degradation of the waste activated sludge in order to minimize excess biological waste production.

The system is designed for the retention, hydrolysis and fermentation of solids to provide Chemical Oxygen Demand ("COD") for denitrification, oxidation of BOD, and nitrogen and nitrogen removal be nitrification. The anaerobic digestion system 120 may include both an anaerobic digester with an insulated cover, a nitrification pond, (aerobic) and a denitrification/irrigation storage pond (anoxic), connected in series. The anaerobic digester can be any conventional digestion apparatus, preferably a sealed apparatus with an insulated cover, such as those disclosed in U.S. Pat. No. 4,372,856, the disclosure of which is incorporated by reference herein in its entirety. The anaerobic digestion system 120 can be designed to accommodate any size facility, or to treat waste from a plurality of farms. Using the guidelines provided herein, and given the predicted tonnage of agricultural waste to treat, those skilled in the art are capable of designing a suitable anaerobic digestion system 120, for use in connection with the system described herein.

Integration with the steam reforming apparatus 140 allows the transfer of excess thermal energy from the reformer to the digester in order to achieve a stable operating temperature of >35° C. within the reactor. Parasitic energy load of the unit typically consists of electric motors driving the submerged mechanical mixer in the digester, the rotary vane blower for biogas harvesting, a single centrifugal pump controlling the feeding of the digester, and the discharge of the sludge/solids from the digester. This load can be accommodated by the heated air turbine electricity generation apparatus 145, if desired. In addition, the anaerobic digestion system 120 may include a system for withdrawing ammonia from the system to be used in cleaning the biogas in the solvent vessel 130 where $H_2S$ is scrubbed from the biogas.

The harvested biogas 122 from the anaerobic digestion system 120 preferably is conveyed to the battery limits of the alcohol conversion apparatus 150 (via solvent vessel 130 and steam reforming apparatus 140) by means of interconnected piping of high density polyethylene (HDPE) or similar non-corrosive materials preferably installed on a downward gradient to allow flow of both gaseous and aqueous phases, including condensate, of the biogas stream. Pumps can be used to pump the respective streams to their destination, if needed, and skilled artisans are capable of designing a suitable mode of transfer using the appropriate piping, gradient, and pumps.

The harvested biogas 122 then is fed to solvent vessel 130 to remove impurities, such as $H_2S$, and the like. Biogas stream 122 typically will contain from about 45% to 90%, more preferably from about 60% to 75%, and most preferably from about 65% to about 70% $CH_4$ and from about 10% to about 55%, more preferably from about 25% to about 40%, and most preferably from about 30% to about 35% $CO_2$ with additional impurities. The biogas 122 usually is received from anaerobic digestion system 120 at atmospheric pressure and ambient temperature.

Figure 2:
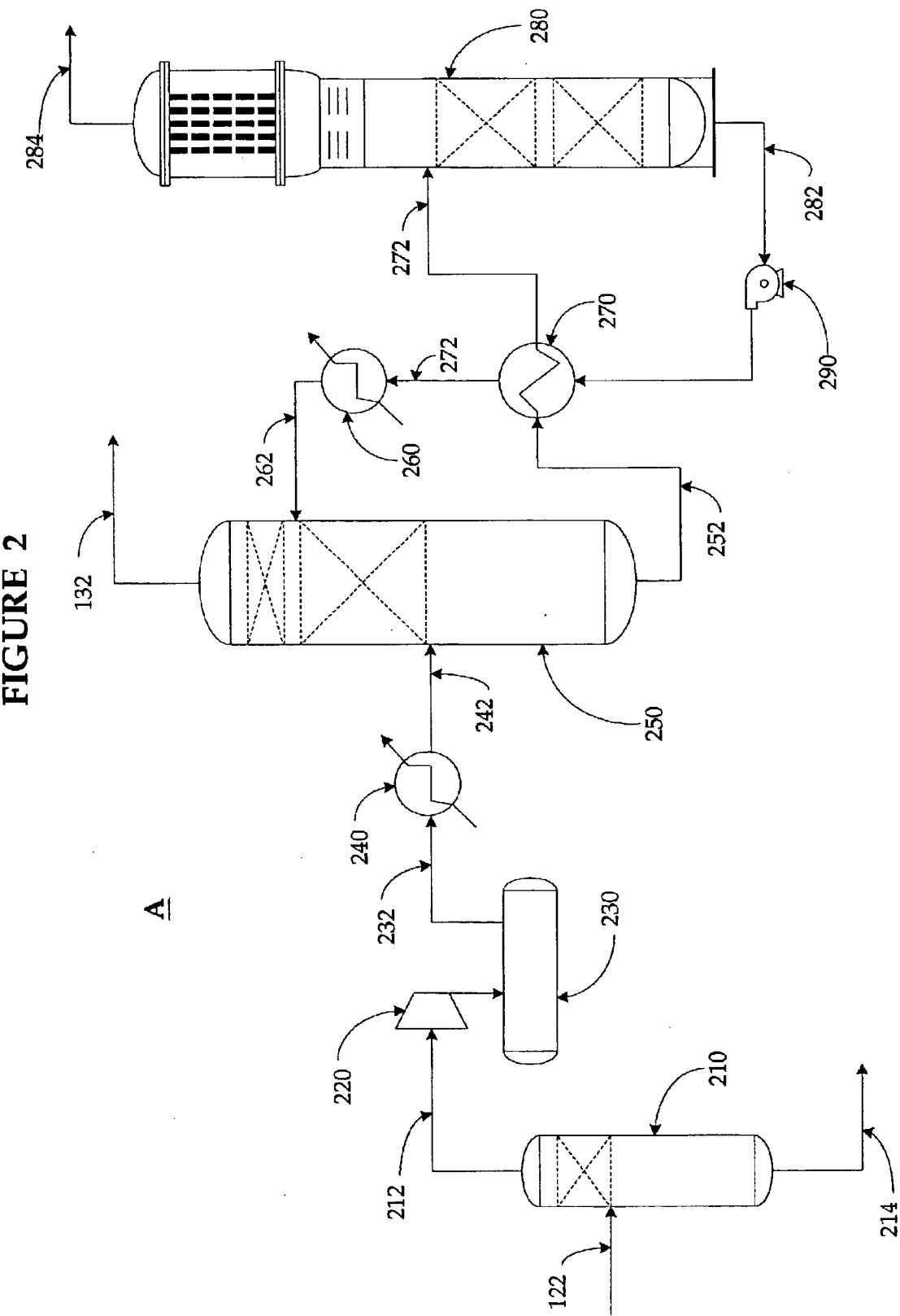
FIG. 2 is a more detailed representation of "A" in FIG. 1, and is a flow diagram of a preferred method of purifying the biogas produced in the digester.

FIG. 2 depicts a more detailed and preferred arrangement for purifying biogas 122, as shown by the letter A in FIG. 1. As shown in FIG. 2, the biogas 122 preferably first passes through an inlet separator 210 where any moisture that has condensed is removed. Any gas/liquid separation apparatus may be used as inlet separator 210 to separate water as condensed moisture via stream 214 from the remaining biogas 212. The biogas 212 then is compressed by a feed gas compressor 220 to 200 psig. Feed gas compressor 220 preferably is integral with in an oil flooded, helical rotary screw type compressor 230. The hot, compressed gas 232 then is cooled in the feed gas aftercooler 240 by exchanging heat with cooling water and any condensed water may be removed in an aftercooler separator, (not shown).

The cooled biogas 242 then passes through an $H_2S$ absorber 250 to remove hydrogen sulfide to the ppm levels. Any type of $H_2S$ absorber 250 can be used so long as it effectively removes hydrogen sulfide from a methane-containing biogas stream. It is particularly preferred in the invention to remove the hydrogen sulfide by direct contact with a physical absorbent, methyldiethanolamine ("MDEA"). The MDEA preferably is contained in a 50% by weight solution and contains enhancements for $H_2S$ selectivity (such as Huntsman chemicals MS-300). The biogas flows upward through a packed column in absorber 250 and directly contacts the amine falling down through the column, which enters the column 250 via amine stream 262. The basic process involved can be summarized as:

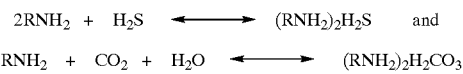

Rich amine, saturated with acid gas, leaves the bottom of the absorber 250 via stream 252 using level control and exchanges heat with hot, lean amine in the lean/rich heat exchanger 270. From the lean/rich heat exchanger 270, the rich amine 272 enters the top of the $H_2S$ stripper 280. The amine solution flows downward through a packed section of the column where it is heated by hot rising vapors generated in the $H_2S$ stripper reboiler (not shown). Steam preferably is used as the heat media for the reboiler. Acid gas liberated from the amine solution and a portion of the internally generated stripping steam are carried overhead into the $H_2S$ stripper overhead condenser where the steam is condensed and cooled by exchanging heat with cooling water. The condensed steam falls back down the column thus providing reflux for the stripper. The cool acid gas ($H_2S$ & $CO_2$) from the top of the column is routed for incineration via stream 284.

Hot, lean amine 282 from the bottom of the stripper 280 then preferably is pumped via the lean amine pump 290 through the lean/rich exchanger 270 and then through the lean amine cooler 260 where the amine is cooled to approximately 100° F. by exchanging heat with cooling water. A portion of the amine may be filtered with an amine filter (not shown), if desired. The cool, filtered amine then enters the top of the absorber 250 via stream 262 to complete the cycle.

Biogas exits the top of the absorber 250 via stream 132 and then can be routed to the reformer for reformation into carbon dioxide and hydrogen syngas. An alternative to the embodiment depicted in FIG. 2 for stripping the $H_2S$ from the biogas would be to use ammonia generated and collected from the anaerobic digestion system 120 as the stripping amine solution, as described in U.S. Pat. No. 4,372,856. The clean biogas stream 132 containing methane and carbon dioxide, with trace if any, amounts of $H_2S$, then is fed to the steam reformer apparatus 140, where it is converted to a syngas containing carbon monoxide and hydrogen. The steam reformer apparatus also may include an electricity generator apparatus 145 to generate electricity for use in the overall process.

Figure 3:
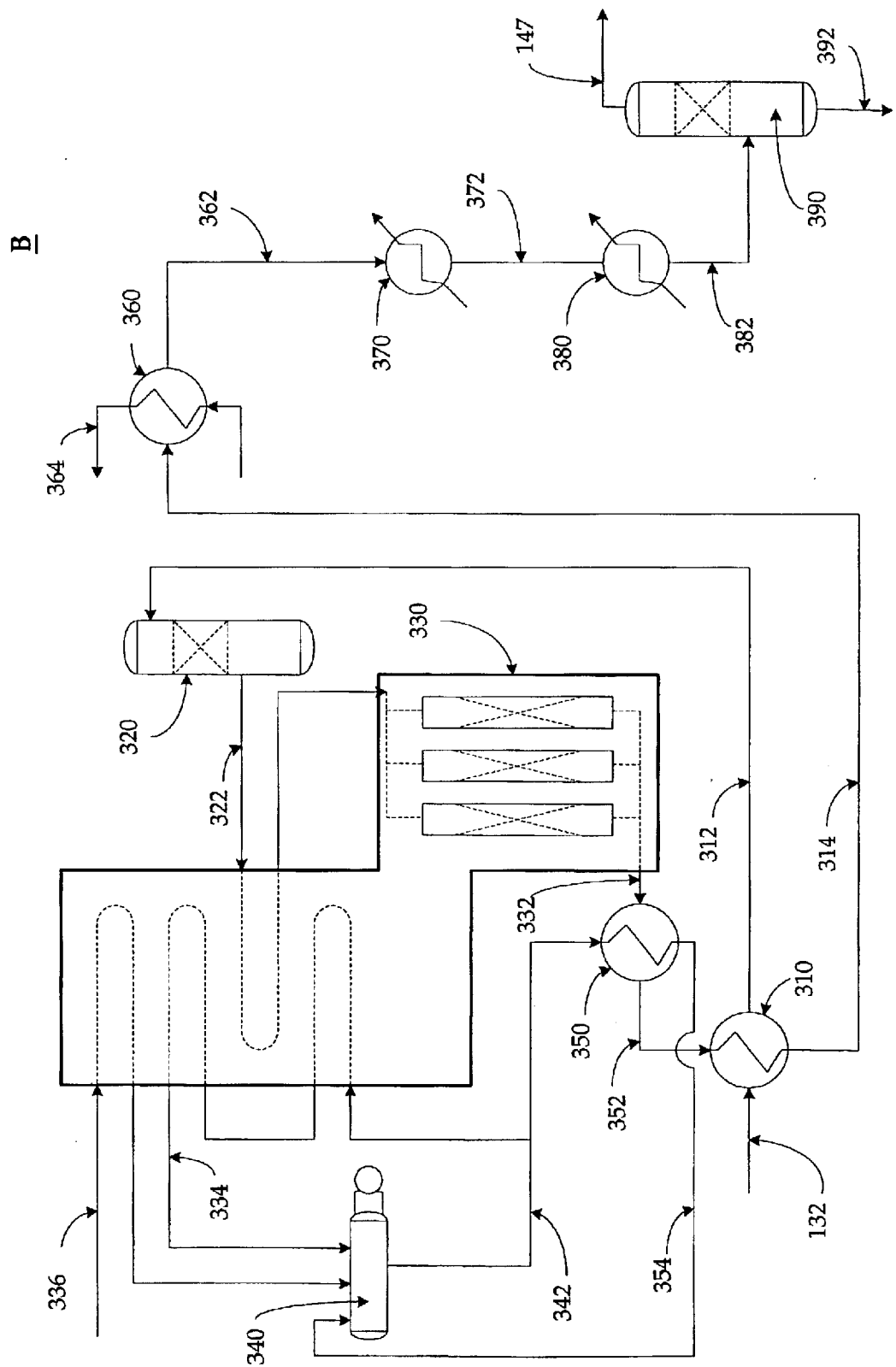
FIG. 3 is a more detailed representation of "B" in FIG. 1, and is a flow diagram of a preferred method of reforming the biogas into a syngas.

A more detailed preferred embodiment of the steam reformer apparatus is shown in FIG. 3. As shown in FIG. 3, cleaned biogas stream 132 is heated in an inlet gas heater 310, preferably to approximately 600–800° F., and more preferably to about 700° F. by exchanging heat with hot syngas stream 352 exiting the waste heat boiler 350 and reformer 330. The hot biogas then passes through a packed bed column 320, preferably containing zinc oxide, where any traces of $H_2S$ are removed preferably down to the 0.1 ppm levels by the zinc oxide.

Hot, purified biogas stream 322 then is mixed with steam and enters the reformer 330. Reformer 330 can be any reformer capable of converting, or "reforming" the biogas containing methane and carbon dioxide to carbon monoxide and hydrogen. In a most preferred embodiment, reformer 330 is a direct-fired heater that contains furnace tubes that are filled with a nickel catalyst. The predominant reaction that takes place is the steam reforming of methane:

$$CH_4 + H_2O \longleftrightarrow CO + 3H_2$$

This reaction is endothermic and conversion is enhanced by high temperature, low pressure and high steam to carbon ratios. In addition to the reforming reaction to produce carbon monoxide and hydrogen, the following water gas shift reaction takes place:

$$CO + H_2O \longleftrightarrow CO_2 + H_2$$

This water gas shift reaction is exothermic and the amount of carbon dioxide formed is determined by the reaction equilibrium at the outlet conditions of the reformer 330. High temperatures cause the reaction to shift to the left and high water concentrations cause the reaction to shift to the right. Traditionally, synthesis gas for methanol production was carbon-oxide short and the net result was an excess of hydrogen. Therefore, many methanol facilities were forced to add $CO_2$ to the feed (1 mole $CO_2$ for every 4 moles $CH_4$). Since the biogas contains carbon dioxide, the overall stoichiometric ratio, $R=[H_2/(2CO+3CO_2)]$ is closer to unity. It therefore is particularly preferred in the present invention that no additional carbon dioxide is added to convert the biogas to carbon monoxide and hydrogen in reformer 330, although some carbon dioxide could be added if needed.

The radiant box of the reformer 330 typically is approximately 50% efficient. In order to ensure a thermodynamically efficient operation, the heat unabsorbed by the reforming reaction can be recovered in the convection section of the furnace (the upper portion of reformer 330). The high temperature flue gases pass upward through the convection section to generate steam in steam drum 340 which is fed by steam lines 336, 334, 354. The steam so generated then can be used for heat in the process, which brings the overall furnace efficiency close to 90%.

Hot syngas exits reformer 330 via hot syngas stream 332. The temperature and pressure of hot syngas stream 332 will depend on the operating conditions of reformer 330, and the make up of hot purified biogas 322 entering reformer 330. In preferred embodiments, hot syngas stream 332 exits reformer 330 at about 1200 to about 200° F. and from about 150 to about 200 psig, more preferably from about 1400 to about 165° F. and from about 170 to about 190 psig, and most preferably, at approximately 1575° F. and 181 psig.

The hot syngas stream 332 then passes through a series of heat exchangers to efficiently cool the gas. First, the hot syngas stream enters the waste heat boiler 350 where the syngas is partially cooled by exchanging heat with water stream 342 to generate steam stream 354, which then is fed back to steam drum 340 The syngas then passes through the tube side of the inlet gas heater 310 to preheat the cleaned biogas stream 132. The syngas stream 314 then flows through the refining column reboiler 360 to provide heat for methanol distillation, de-aerator preheater 370 to heat the boiler feed water and finally through the syngas cooler 380 where the syngas is cooled to about 75 to about 150° F., preferably to about 100° F. by exchanging heat with cooling water. The cooled syngas stream 382 may contain some condensed water. Excess water condensed in the exchangers in cooled syngas stream 382 then is separated from the gas stream in the syngas condensate separator 390 to produce cooled syngas stream 147 and water 392. The syngas at this point preferably includes the following constituents: The mole percentages listed in the table below are estimated percentages based on a typical manure feed. Those skilled in the art will appreciate that treating different agricultural waste streams will generate a cooled syngas stream 147 containing essentially the same components, but the amounts may vary.

| Component | Mole % |
| --- | --- |
| Hydrogen | 68.47 |
| Methane | 0.83 |
| Carbon dioxide | 12.94 |
| Carbon monoxide | 16.60 |
| Water | 0.47 |
| Nitrogen | 0.69 |

Figure 4:
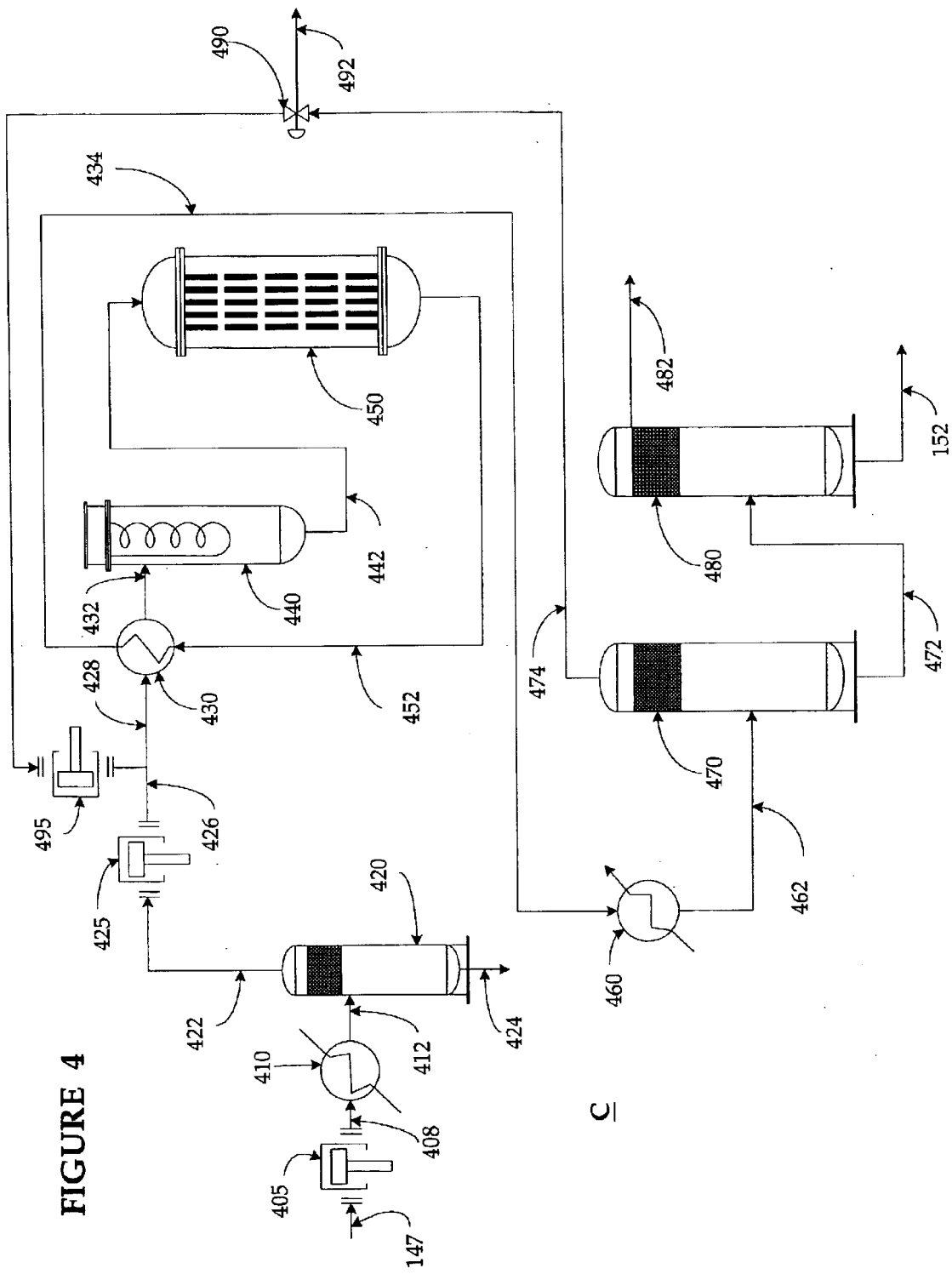
FIG. 4 is a more detailed representation of "C" in FIG. 1, and is a flow diagram of a preferred method of converting the syngas into methanol.

Cooled syngas stream 147 preferably enters alcohol conversion apparatus 150 at about 100° F. and about 168 psig. A more detailed and preferred depiction of alcohol conversino apparatus 150 is shown in FIG. 4. Referring now to FIG. 4, cooled syngas stream 147 is compressed to converter pressure (preferably, approximately 950 psi) by the syngas compressor 405. Any compressor can be used as syngas compressor 405, and preferably, syngas compressor 405 is a two stage, reciprocating compressor. Between stages, the compressed syngas 408 preferably is cooled by the syngas intercooler 410 by exchanging heat with cooling water and any condensate formed is removed by the syngas interstage separator 420 to form compressed syngas stream 422 and water stream 424. Compressed syngas stream 422 is compressed in second stage compressor 425 to form a hot, compressed syngas stream 426, which then may be mixed with recycle gas from the recycle compressor 495 discharge to form combined hot syngas stream 428. Combined hot syngas stream 428 then flows through the syngas loop exchanger 430 where the combined hot syngas stream 428 exchanges heat with the converter effluent stream 452 bringing the gas stream up to reaction temperature. The reaction temperature for conversion to methanol preferably is within the range of from about 350 to about 550° F., more preferably from about 400 to about 500° F., and most preferably about 450° F. The hot syngas stream 432 then passes through the start-up heater 440, preferably an electric resistance heater, that is used only during start-up to bring the hot syngas stream 432 up to reaction temperature.

The heated syngas stream 442 then enters the methanol converter 450. Any apparatus capable of converting carbon monoxide and hydrogen to methanol can be used in the invention. Preferably, the methanol convertor 450 is a reactor with a pseudo-isothermal design having a catalyst contained in the tubes of the converter 450. The heated syngas stream 442 syngas passes down through a bed of catalyst, preferably a Cu—Zn catalyst, and the primary reaction that takes place is:

$$CO + 2H \longleftrightarrow CH_3OH \quad \Delta H = 39{,}020$$

This reaction is exothermic with the equilibrium concentration of methanol affected by the temperature and pressure. Higher pressure and lower temperatures increase the rate of conversion. Another reaction that takes place in the methanol converter 450 is a reverse water-gas shift reaction:

$$CO_2 + H_2 \longleftrightarrow CO + H_2O \quad \Delta H = 17{,}709$$

The reverse shift reaction is endothermic. Both the reverse shift and the methanol reaction take place simultaneously with the net results being exothermic. Other hydrocarbon byproducts may be formed as well (e.g., higher alcohols, dimethyl ether, methyl formate, acetones and ketones, etc.), but typically are present in concentrations of less than 5000 ppm.

As the reactions take place in the tubes, the heat generated by the reactions is removed by exchanging heat with boiling water on the shell of the reactor. The methanol content of the converter effluent stream 452 preferably is about 4 to about 10%, and most typically is approximately 7%. The converter effluent stream 452 also typically will have a temperature within the range of from about 400 to about 550° F., and most typically approximately 485° F. Converter effluent stream 452 enters the tube side of syngas loop exchanger 430 where the cooled converter effluent stream 434 is cooled to about 150 to about 300° F., preferably, about 211° F. by exchanging heat with the reactor feed. The cooled converter effluent 434 then passes through a methanol condenser 460 where methanol and water are condensed by exchanging heat with cooling water. Condensed methanol stream 462, which contains water then is separated from the gas stream in the methanol separator 470. The remaining gas stream 474 then is routed to the recycle compressor 495 where the gases are recompressed to pass through the synthesis loop again. Since stoichiometric feedstocks are seldom achieved, some of the gas can be purged from the loop via valve 490 to reduce the buildup of the excess constituents and the methane and nitrogen buildup in the loop. The loop purge stream 492 preferably is routed to the reformer 330 (FIG. 3) as fuel.

Crude methanol stream 472 from the methanol separator 470 then preferably enters a methanol letdown drum 480 via level control for degasification. Vapors generated in the letdown are sent to fuel as stream 482 and the methanol then is routed to distillation unit 160 (FIG. 1) via methanol stream 152.

Figure 5:
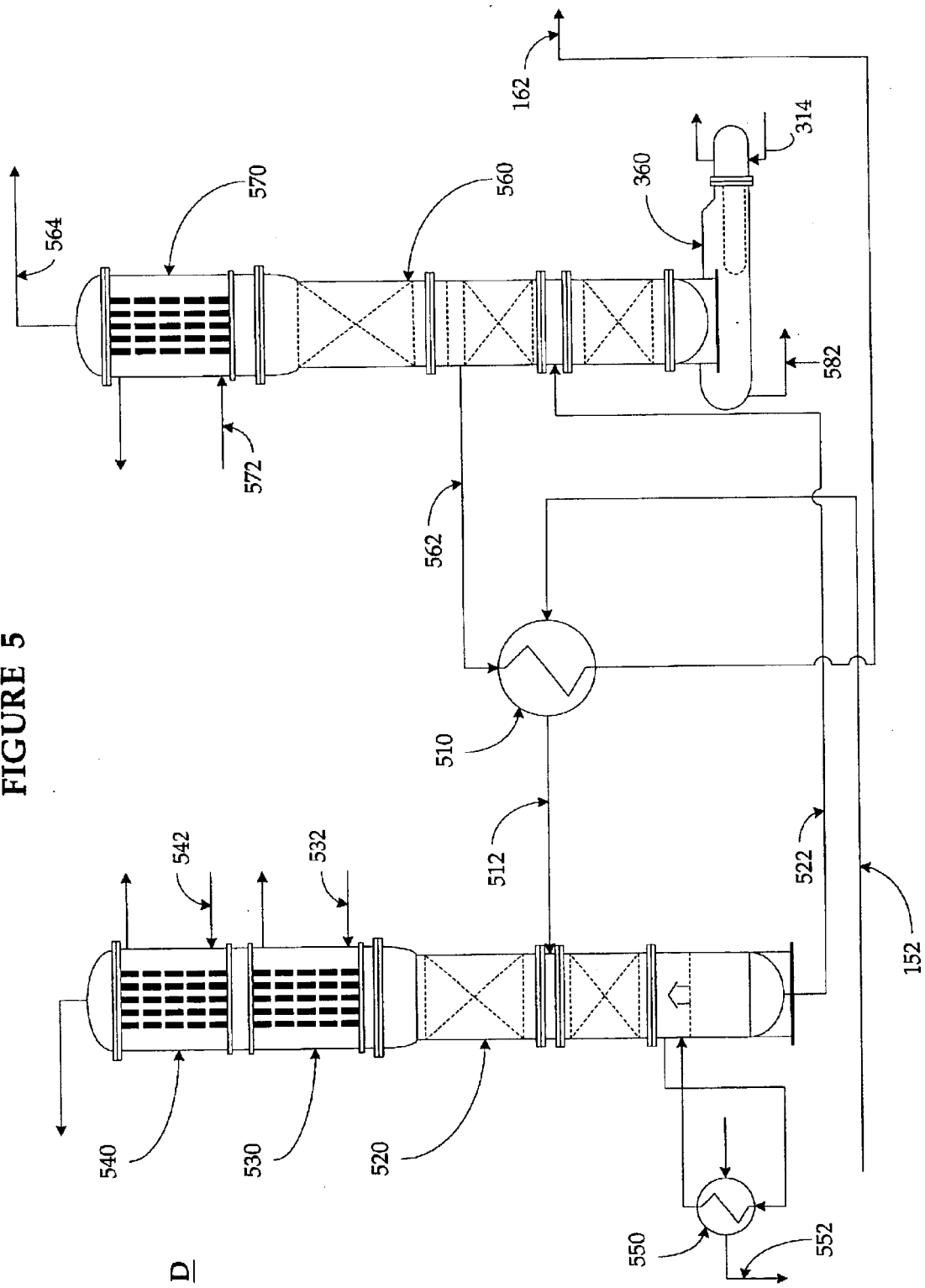
FIG. 5 is a more detailed representation of "D" in FIG. 1, and is a flow diagram of a preferred method of distilling the methanol.

A more detailed and preferred depiction of distillation unit 160 is shown in FIG. 5. As shown in FIG. 5, methanol preferably is distilled by a two-column system, although any distillation unit 160 suitable for separating methanol from water and other components in methanol stream 152 can be used in the invention. The fractionation is conventional with the first column 520 removing those constituents boiling at a temperature lower than that of methanol. The second column 560 separates the methanol from the water.

Methanol stream 152 preferably is heated in a product cooler 510 by exchanging heat with product methanol stream 562. The heated methanol 512 then enters the topping column 520 for light ends removal. Heat is provided to the column by steam in the topping column reboiler 550. Vapors generated in the topping column reboiler 550 strip the light ends from the liquid falling through the column packing. Column reflux preferably is provided by the topping column reflux condenser 530 by exchanging heat with cooling water 532. Vapors leaving the reflux condenser 530, preferably at approximately 146° F. and 20 psig, may contain ethanol. Most of the methanol is recovered in the purge condenser 540 by further cooling with cooling water 542.

The "topped" methanol that exits from the bottom of the topping column 520 via stream 522 then preferably is pumped (pump not shown) to the refining column 560. Heat for the refining column is provided by the refining column reboiler 360 utilizing hot syngas stream 314 from the reformer 30 (FIG. 3). The product methanol stream 562 is removed just below the refining column reflux condenser 570. The refining column reflux condenser 570 provides reflux to the column by exchanging heat with cooling water 572. Uncondensed vapors, preferably at about 157° F. and 3 psig are purged from the column via stream 564 and routed to fuel. Water from the bottom of the column is routed to the de-aerator via stream 582. The methanol product stream 562 from the refining column is cooled in the product cooler 510 and then either stored via stream 164 in storage tank(s) 190 (FIG. 1), directly sent to heated reactor 170 via stream 162 for conversion into biodiesel, or both.

Biodiesel can be produced from the methanol product stream 162 using conventional methods, including those disclosed in U.S. Pat. Nos. 5,713,965, 6,015,440, and 6,440,057, the disclosures of which are incorporated herein by reference in their entirety. Referring again to FIG. 1, methanol product stream 162 typically is mixed with natural fats and/or oils in a heated reactor 170 to form glycerine or glycerol and methyl esters via a transesterification process. The transesterification product stream 172, which contains the glycerol, (and/or glycerine) and methyl ester, then is sent to separator 180 whereby the insoluble glycerine products settle out through glycerine product stream 184, and methyl esters are drawn off the top via methyl ester product stream 182. The methyl ester then can be used directly as a biodiesel fuel, or mixed with other fuels.

In a particularly preferred embodiment of the invention, the process of converting methanol into biodiesel involves the esterification of free fatty acids and the reesterification of triglycerides or glycerol esters of fatty acids into methyl esters of fatty acids in the presence of an alkaline catalyst. The basis of the procedure is the reduction of molecule mass and, by that, a reduction of viscosity and boiling point such that the monoalkyl esters or methyl ester may replace petroleum diesel in compression-ignition engines without mechanical alterations to the engines. Alternatively, the monoalkyl esters may be utilized directly in the petrochemical and pharmaceutical industries as a precursor to other products.

The mass balance for producing the monoalkyl ester is:
100 kg of a fat or oil+15 kg of methanol+1 kg of KOH or NaOH=100 kg of biodiesel (methyl esters)+10 kg of impure glycerin Although not shown in FIG. 1, the production of the monoalkyl ester preferably takes place in a two-stage alkaline esterification/reesterification process. In the first stage, the low humidity methanol product 162 is contacted with an alkaline (not shown) to prepare a methoate. Preferably, the methoate is prepared from a solid granular catalyst blended with methanol in a stirred dissolving tank (not shown) at a process temperature of about 55° C. The methoate then is directly blended with an oil source such as tallow and the like via stream 171, at the same temperature in a continuously stirred, heated reactor 170. The reaction preferably takes place at or about 55° C.

The resulting transesterification product stream 172, typically in the form of an emulsion, then is pumped to a static phase separator 180 and optionally cooled to about 38° C. The separation preferably creates a clean separation between the hydrophobic phase (monoalkyl esters), which can be drawn off the top as the methyl ester product stream 182, and the hydrophilic phase (glycerol, water, methanol, catalyst, soap and methylesters), which is withdrawn from the bottom of the separator 180 as glycerine product stream 184.

The raw glycerine product stream 184 preferably is warm water washed, and then placed under vacuum to remove excess methanol, which can be recycled to the initial 1$^{st}$ stage reactor. The hydrophobic phase, or methyl ester product stream 182, then preferably is pumped from the separator 180 to an intermediary stirred vessel (not shown) where a secondary catalyst can be added to remove color from the monoalkyl ester and reduce viscosity. The product from the intermediary stirred vessel then can be pumped to a distillation column (not shown) where retained water is removed by vacuum distillation. The final monoalkyl ester product then can be pumped to a final product storage tank for use or sale.

In accordance with particularly preferred embodiments of the invention, the resulting monoalkyl ester product has the characteristics shown in Table 1 below:

TABLE 1

| Fuel Property | Biodiesel |
| --- | --- |
| Fuel Standard | ASTM 6595 |
| Fuel Composition | C12–C22 FAME |
| Lower Heating Value, Btu/gal | 117,093 |
| Kin. Viscosity, @40° C. | 1.9–6.0 |
| Specific Gravity kg/l @ 60° F. | 0.88 |
| Density, lg/gal @ 15° C. | 7.328 |
| Water, ppm by wt. | 0.05% max |
| Carbon, wt % | 77 |
| Hydrogen, wt % | 12 |
| Oxygen, by dif. wt % | 11 |
| Sulfur, wt % | 0.0–0.0024 |
| Boiling Point, ° C. | 182–338 |
| Flash Point, ° C. | 100–170 |
| Cloud Point, ° C. | −3 to 12 |
| Pour Point, ° C. | −15 to 10 |
| Centane Number | 48–65 |
| Stoichiometric Air/Fuel Ratio | 13.8 |
| BOCLE Scuff, grams | >7,000 |
| HFRR, microns | 314 |

The crude glycerol phase of approximately 10% by weight of the input oil also may be pumped to a separate distillation column for neutralization by addition of phosphoric acids, and the like, and removal of water, methanol for recycling, alkalis, methylesters and reduction of color. The product of this process then can be pumped to a storage vessel for sale.

As part of, or adjacent to the steam reformer apparatus 140 is an electricity generating apparatus 145 which produces electricity for sale and/or use throughout the process. Any electricity generating apparatus 145 can be used in the present invention, including those disclosed, for example, in U.S. Pat. Nos. 5,121,600 and 6,410,283, the disclosures of which are incorporated by reference herein in their entirety. Preferably, the electric generation apparatus 145 is an air turbine unit, e.g., an "open" Brayton Cycle—using air as the working fluid, which is heated via a series of heat exchangers in the steam reformer 330. The primary benefits of this system include a reduction in turbine maintenance because air is the working fluid, fuel flexibility, and a relatively small (e.g., 300 kW) size, which lends itself to modular construction and transportability.

Figure 6:
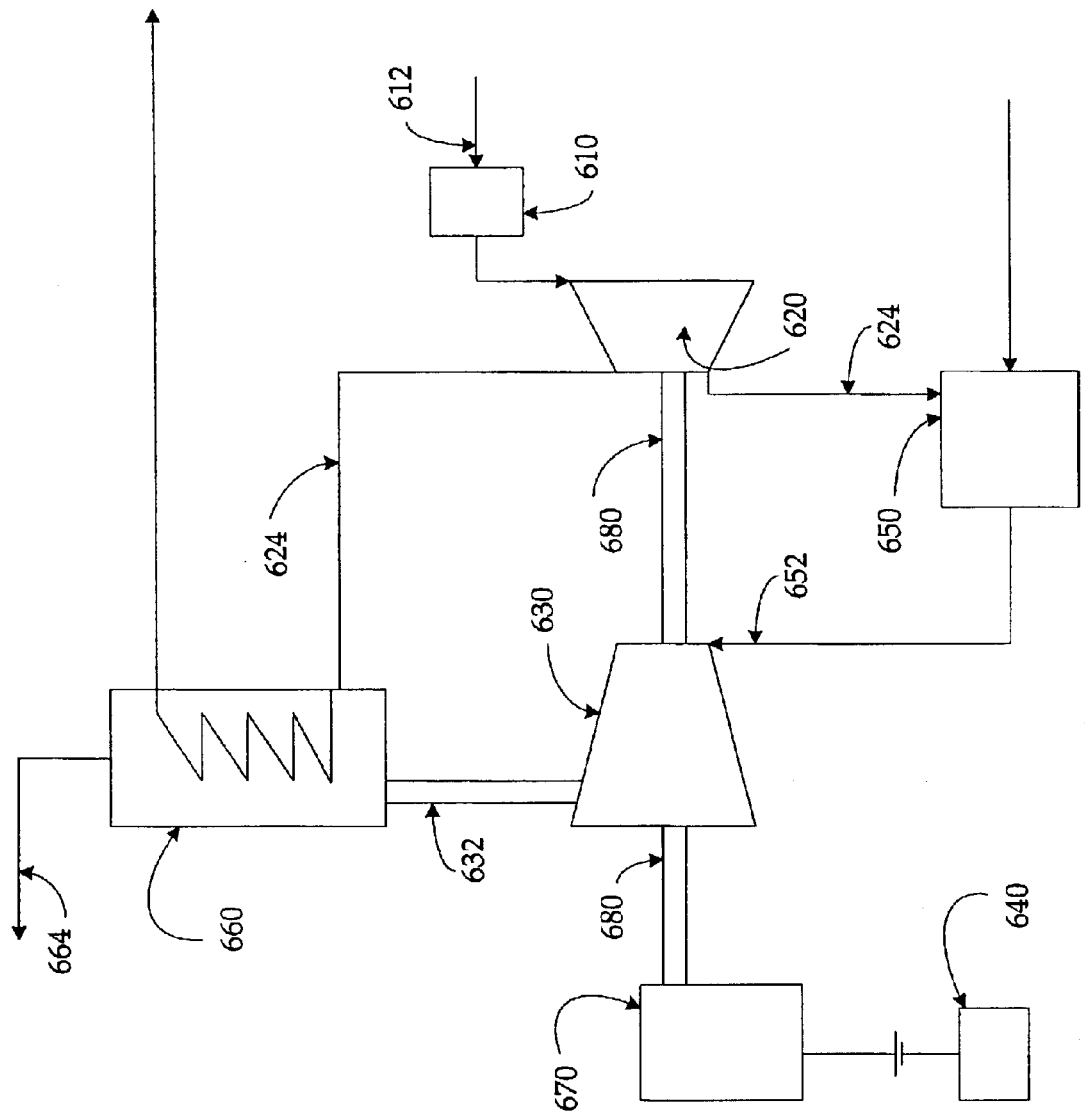
FIG. 6 is a more detailed representation of an air turbine electric generator useful in generating electricity from the process of the invention.

The present invention encompasses the use of a gas turbine engine of a conventional type manufactured by a number of established entities. An exemplary embodiment is illustrated in FIG. 6. Turning now to FIG. 6, the electricity generation unit 145 may include a compressor 620 that has an atmospheric air inlet and compressed air outlet. The atmospheric air is drawn into the compressor 620 via air stream 612 on the suction side, preferably through a replaceable air filter 610 for removal of particulate matter. The inlet air is compressed by the turbine engine 630 driving a common shaft 680 with the electrical generator 670 and exits the compressor at the outlet. The compressed air may optionally pass through a convection heat exchanger, or recuperator, (not shown) that can raise the temperature and pressure of the air by withdrawal of heat from the exhaust stream of the turbine engine, without intermixing of the fluids.

The heated, compressed air also may continue through an insulated flow line to a convective heat exchanger (not shown) that withdraws additional heat from the cross-exchange with the outlet syngas of the reformer 330 (FIG. 3). The heated, compressed air passes through an insulated flow line 624 to a combustion apparatus 650. The temperature of the inlet stream of heated, compressed air into the device preferably is monitored in real time by a controller 640. If insufficient thermal energy is contained in the operating fluid, controller 640 will introduce a measured amount of ignitable fluid into the combustion apparatus 650 on a temporary basis in order to achieve the minimum operating temperature of the operating fluid to drive the turbine engine or for a black start. The heated, compressed air passes through an insulated flow line 652 to the inlet of the turbine engine 630.

The heated, compressed air expands across the turbine blades of the turbine engine causing a common shaft 680 to drive both the compressor 620 and the electrical generator 670. The exhaust of the turbine engine passes via turbine exhaust stream 632, preferably an insulated flow line, to a recuperator 660 to heat the compressed air from the outlet of the compressor via stream 624. The turbine exhaust stream 632 then is passed into the atmosphere through the exhaust stack stream 664 without further treatment. The electrical energy produced by the electrical generator 670 preferably is produced in a synchronized device for delivery to electrical motors integral to the production process or for export into a utility grid.

By way of example only, an exemplary system designed to produce approximately 200 kW gross and employing a turbine engine would require an air mass flow of about 2.75×10 Btu/hr net thermal energy. The inlet atmospheric air could be compressed to 5 lbs/sec (60 psia) and heated from about 77° F. to about 418° F. by compression alone. The compressed air stream would enter the recuperator 660 attached to the turbine engine exhaust stream 632 and be cross heat exchanged with the turbine engine exhaust to about 1045° F. and remain at 5 lbs/sec. The turbine engine exhaust stream 632 would enter the recuperator 660 at about 1125° F. and leave at about 504° F., giving rise to a heat exchange value of E=0.88%. The heated, compressed air stream would enter the convective heat exchanger of the reforming loop (FIG. 3) at 5 lbs/sec and cross exchange with the intercooling system in order to elevate the air temperature to >1350° F. at a pressure of 58 psia for introduction into the combustion apparatus 650. The controller 640 would sample the inlet heated, compressed air for temperature and pressure and introduce ignitable fluid sufficient to achieve the minimum thermal energy within the operating fluid to drive the turbine engine. The expansion of the operating fluid across the turbine engine drives the generator at E=0.85%. The produced electric load is directed to a turbine control synchronizer for reliable export capability.

While the invention has been described with reference to particularly preferred embodiments and examples, those skilled in the art will appreciate that modifications may be made without departing from the spirit and scope of the invention.

What is claimed is:

1. A method for treating agricultural wastes comprising:
    anaerobic digesting a mixture of at least agricultural waste and water to yield solids and a biogas including methane and carbon dioxide;
    reforming the biogas including methane and carbon dioxide to a syngas including carbon monoxide and hydrogen in a steam reformation process;
    converting the syngas containing carbon monoxide and hydrogen to methanol in an alcohol conversion process;
    contacting at least a portion of the methanol with natural fats and/or oils in a transesterification reactor to form glycerine and methyl esters; and
    separating the glycerine from the methyl ester.

2. The method according to claim 1, wherein the anaerobic digesting compriss digesting concentrated agricultural waste having a solids content of greater than about 4–8% that is heated prior to digestion.

3. The method according to claim 1, wherein prior to anaerobic digestion, the agricultural waste is concentrated up to about 30% solids, the concentrated agricultural waste then is contacted with water to produce an agricultural waste stream having a solids content from about 4% to about 8%.

4. The method according to claim 1, wherein the anaerobic digesting has a retention rime of less than about 30 days.

5. The method according to claim 1, wherein the agricultural waste is comprised primarily of animal manures.

6. The method according to claim 1, wherein the biogas produced by anaerobic digestion is purified to form a cleaned biogas stream prior to reforming.

7. The method according to claim 6, wherein the biogas is purified by passing the gas through a solvent vessel to remove entrained $H_2S$.

8. The method according to claim 7, wherein the biogas is purified by:
    separating entrained moisture from the biogas by passing the gas through an inlet separator;
    compressing the separated gas in a feed gas compressor to form a compressed gas stream; and
    removing hydrogen sulfide in a hydrogen sulfide absorber wherein the compressed gas stream is contacted with methyldiethanolamine to produce a cleaned biogas stream.

9. The method according to claim 1, wherein reforming the biogas comprises:
    heating the biogas;
    reforming the biogas by mixing the heated biogas with steam in the presence of a catalyst to form a hot syngas stream; and
    cooling the hot syngas stream to form a syngas stream.

10. The method according to claim 9, wherein the syngas stream comprises about 69 mol% hydrogen, about 13 mol % carbon dioxide, and about 17 mol % carbon monoxide.

11. The method according to claim 1, wherein converting the syngas to methanol comprises:
    compressing the syngas to form a hot, compressed syngas stream;
    converting the hot, compressed syngas into methanol in a methanol converter to form a hot methanol stream; cooling the hot methanol stream to form a condensed methanol stream; and
    separating condensed methanol from gas in a methanol separator.

12. The method according to claim 11, wherein additional carbon dioxide is not added to convert the syngas into methanol.

13. The method according to claim 11, wherein the methanol converter is a catalytic reactor containing a catalyst selected from $ZnO-Cr_3O_3$ and $CuO-ZnO-Al_2O_3$.

14. The method according to claim 1, wherein at least a portion of the solids remaining after anaerobic digestion are removed and treated to form fertilizer.

15. A system for treating agricultural waste comprising:
    an anaerobic digestion apparatus to digest agricultural waste and create solids and a biogas;
    a biogas reformation apparatus to reform the biogas into a syngas comprising carbon monoxide and hydrogen;
    and an alcohol conversion apparatus to convert the carbon monoxide and hydrogen into methanol;
    transesterification reactor to react at least part of the methanol with natural fats and/or oils to form glycerine and methyl esters; and
    a separation apparatus to separate the glycerine from the methyl esters.

16. The system according to claim 15, further comprising a biogas purification system, the biogas purification system comprising:
    an inlet separator to separate entrained moisture from the biogas;
    a feed gas compressor to compress the separated gas and to form a compressed gas stream; and
    a hydrogen suit tie absorber to remove hydrogen sulfide by contacting the compressed gas stream with methyldiethanolamine to produce a cleaned biogas scream.

17. The system according to claim 15, wherein the biogas reformation apparatus comprises:
    a heater to heat the biogas;
    a reformer to reform the biogas by mixing the heated biogas with steam in the presence of a catalyst to form a hot syngas stream; and
    a heat exchanger to cool the hot syngas scream with compressed air to form a syngas stream and a hot air stream.

18. The system according to claim 17, wherein the biogas reformation apparatus further includes an electricity generating apparatus.

19. The system according to claim 18, wherein the electricity generating apparatus comprises:
- a compressor to compress the hot air stream from the heat exchanger
- a turbine engine connected to the compresseor and to an electrical generator by a common shaft;
- a combustion apparatus connected to the compressor and turbine engine to provide hot compressed air to the turbine engine; and
- an electrical generator connected to the turbine engine by the common shaft.

20. The system according to claim 15, further comprising a distillation unit to distill the methanol product.

21. The system according to claim 20, wherein the distillation unit comprises a two-column distillation system comprising:
- a product cooler to heat the methanol with a product methanol stream;
- a tapping column to remove lights, the topping column comprising a column reflux condenser, and a purge condenser; and
- a refining column to produce a product methanol stream, the refining column comprising at least a refining reflux condenser.

* * * * *